(12) United States Patent
Meulener

(10) Patent No.: US 7,544,060 B2
(45) Date of Patent: Jun. 9, 2009

(54) DENTAL DEVICE FOR REGISTRATION OF MIDLINE AND HORIZONTAL PLANE

(76) Inventor: Carlos Meulener, 523 Seven Bridges Rd., Little Silver, NJ (US) 07739

( * ) Notice: Subject to any disclaimer, the term of this patent is extended or adjusted under 35 U.S.C. 154(b) by 289 days.

(21) Appl. No.: 11/157,518

(22) Filed: Jun. 21, 2005

(65) Prior Publication Data

US 2006/0210946 A1  Sep. 21, 2006

Related U.S. Application Data

(60) Provisional application No. 60/662,262, filed on Mar. 16, 2005.

(51) Int. Cl.
*A61C 19/04* (2006.01)
(52) U.S. Cl. .............. 433/68; 433/55; 433/71; 433/72; 433/73
(58) Field of Classification Search ........... 433/68, 433/71, 37, 44, 69–72, 54–56, 73
See application file for complete search history.

(56) References Cited

U.S. PATENT DOCUMENTS

| | | | | | |
|---|---|---|---|---|---|
| 1,589,973 | A | * | 6/1926 | Landa | 33/514 |
| 1,830,248 | A | * | 11/1931 | Smith | 433/71 |
| 1,944,601 | A | * | 1/1934 | Gulick | 33/513 |
| 2,310,360 | A | * | 2/1943 | Fischer | 433/71 |
| 2,738,583 | A | * | 3/1956 | Green | 433/69 |
| 3,916,527 | A | * | 11/1975 | Linkow | 433/48 |
| 4,306,861 | A | * | 12/1981 | Dickson | 433/69 |
| 5,028,232 | A | * | 7/1991 | Snow | 433/24 |
| 5,154,609 | A | * | 10/1992 | George | 433/68 |
| 5,722,828 | A | * | 3/1998 | Halstrom | 433/69 |
| 6,190,171 | B1 | | 2/2001 | Hajjar et al. | 433/218 |
| 6,582,931 | B1 | * | 6/2003 | Kois et al. | 435/56 |
| 6,641,340 | B1 | | 11/2003 | Hajjar et al. | 409/94 |
| 6,712,607 | B2 | | 3/2004 | Andreiko | 433/9 |
| 6,786,726 | B2 | | 9/2004 | Lehmann et al. | 433/223 |
| 6,905,337 | B1 | | 6/2005 | Sachdeva | 433/229 |
| 7,364,429 | B2 | * | 4/2008 | Olivier | 433/73 |
| 2006/0188839 | A1 | * | 8/2006 | Adams | 433/68 |

* cited by examiner

*Primary Examiner*—Cris L Rodriguez
*Assistant Examiner*—Hao D Mai
(74) *Attorney, Agent, or Firm*—Porzio, Bromberg & Newman, P.C.

(57) ABSTRACT

The dental device of the present invention is used to transfer information about registration of an anterior midline between central incisors and a horizontal plane of the teeth after the teeth have been drilled and final impressions have been taken. This information is communicated to the lab technician for fabrication of crowns and or veneers. The dental device allows the dentist to consistently communicate the location and position of the anterior midlines and horizontal plane to the dental laboratory. The dental device is placed between the patient's upper and lower teeth after tooth preparation. The dental device is positioned in a correct midline and horizontal plane. After alignment, the dental device is secured to the teeth using a bite registration material. The dental device is forwarded to the lab technician together with the model of the teeth after preparation.

5 Claims, 2 Drawing Sheets

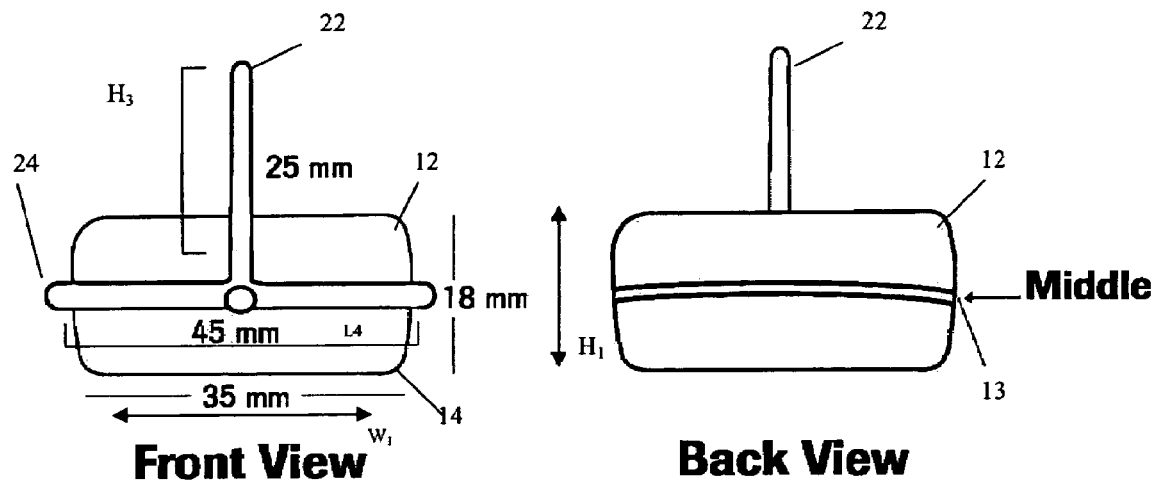
Front View
FIG. 1A
Back View
FIG. 1B
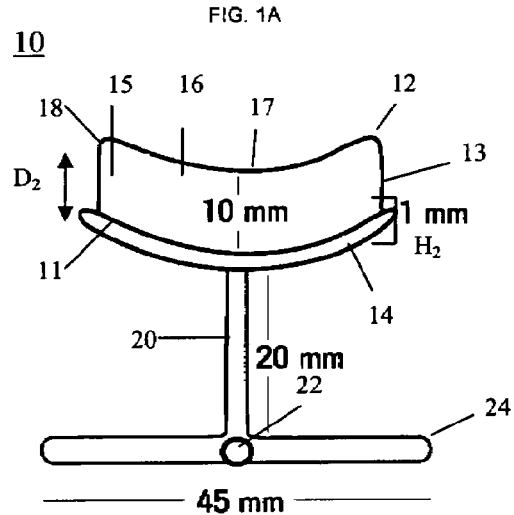
Top View
FIG. 1C

DENTAL DEVICE FOR REGISTRATION OF MIDLINE AND HORIZONTAL PLANE

CROSS REFERENCE TO RELATED APPLICATION

This application claims the benefit of U.S. Provisional Patent Application No. 60/662,262, filed Mar. 16, 2005, the entirety of which is hereby incorporated by reference into this application.

BACKGROUND OF THE INVENTION

1. Field of the Invention

The invention relates to a dental device to make a registration of an anterior midline between central incisors and a horizontal plane during dental treatment.

2. Description of Related Art

During cosmetic dentistry procedures, a dentist typically makes a model of the teeth after preparation. The model is forwarded to a lab technician for forming crowns or veneers to fit with the model. As described in U.S. Pat. No. 6,641,340, once the impression has been produced by the dentist, a laboratory technician will set die pins in the impression and then form a master impression as a die (e.g., plaster models) of the patient's tell. The technician will set the occlusal bite registration and articulate the models of the patient's teeth. Afterwards, the laboratory technician will saw the die to remove the tooth of interest, then trim the die of the tooth and mark the marginal finish line. The sub-structure is then waxed for preparation of the prosthetic crown. After a wax pattern has been formed, it is converted (i.e., cast or machined) into a sub-structure (e.g., coping) of the crown.

It is desirable to provide a device to provide registration of the midline and horizontal plane of the patient to be used with the model to check proper positioning of the crowns or veneers to the model.

SUMMARY OF THE INVENTION

The dental device of the present invention is used to transfer information about registration of an anterior midline between central incisors and a horizontal plane of the teeth after the teeth have been drilled and final impressions have been taken. This information is communicated to the lab technician for fabrication of crowns and or veneers. The dental device allows the dentist to consistently communicate the location and position of the anterior midlines and horizontal plane to the dental laboratory. Applicant is unaware of any other secure method that can accurately transfer this information to be used with the patient's prosthetic dental models.

The dental device is placed between the patient's upper and lower teeth after tooth preparation. The dental device comprises a u-shaped body to fit in a patient's mouth. A bar extends from the front face of the body. A vertical indicator extends vertically from the bar. A horizontal indicator extends horizontally from the bar. The dental device is positioned in a correct midline and horizontal plane using the vertical indicator bar and the horizontal indicator bar. The procedure for positioning the dental device involves using a facial landmark such as the eyes, nose and lips to register the best esthetic position for new crowns or veneers. After alignment, the dental device is secured to the teeth using a bite registration material. The bite registration material can be a fast setting material which is placed on the dental device before positioning in the mouth.

The dental device is forwarded to the lab technician together with the model of the teeth after preparation. The lab technician can then use the dental device to mark on the master model. The lab technician can also check the position of formed crowns or veneers by attaching the formed crowns or veneers to the upper portion of the model and removing the bite registration material from the upper portion of the device. The model and the dental device are closed together on an articulator to see if the midline and horizontal plane are correct before returning the case back to the dentist.

The dental device can be used for the fabrication of crowns and veneers in the anterior dentition. The dental device can also be used in the fabrication of full or partial denture removable prosthetics.

The invention will be more fully described by reference to the following drawings.

BRIEF DESCRIPTION OF THE DRAWINGS

FIG. 1A is a front elevational view of the dental device of the present invention.

FIG. 1B is a back elevational view of the dental device shown in FIG. 1A.

FIG. 1C is a top plane view of the dental device shown in FIG. 1A.

DETAILED DESCRIPTION OF THE PRESENT INVENTION

Figure 2:
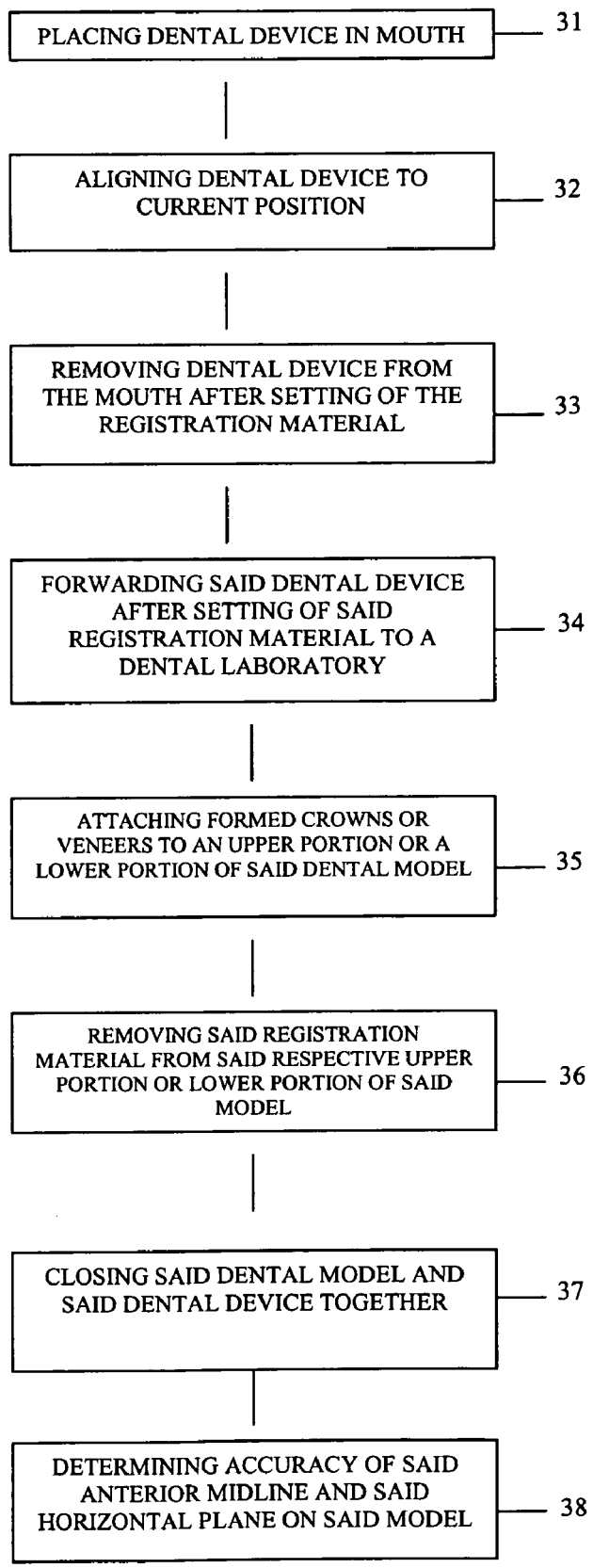
FIG. 2 is a schematic diagram of a method of registration of an anterior midline and horizontal plane using the dental device.

Reference will now be made in greater detail to a preferred embodiment of the invention, an example of which is illustrated in the accompanying drawings. Wherever possible, the same reference numerals will be used throughout the drawings and the description to refer to the same or like parts.

FIGS. 1A-1C illustrate dental device 10 in accordance with the teachings of the present invention. U-shaped body 12 has a curved end 11 with a rounded shape for following the gum line of a patient. Body 12 includes tab stop section 13 extending rearwardly from front face 14 of body 12. For example front face 14 can have a height $H_1$ of about 18 mm and width $W_1$ of about 35 mm for receipt in the patient's mouth. For example tab stop section 13 has a depth $D_2$ of about 10 mm and a height $H_2$ of about 1 mm. It will be appreciated that various sizes of body 12 can be used.

Registration material 15 is placed on upper surface 16 and lower surface 17 of tab stop section 13. Tab stop section 13 can include retaining wall 18 on upper surface and lower surface 17 for retaining registration material 15. Registration material 15 can be formed of a moldable plastic, such as polyvinyl or silicone. A kit can be formed including body 12 and registration material 15.

Bar 20 extends from front face 14 of body 12. Vertical indication bar 22 extends vertically from bar 20. Horizontal indicator bar 24 extends horizontally from bar 20. For example, vertical indicator bar 22 can have a vertical height $H_3$ of about 25 mm and horizontal indicator bar 24 can have a horizontal length $L_4$ of about 45 mm. Vertical indicator bar 22 and horizontal indicator bar can be attached or integrated with bar 20 to form an upside-down "T".

Dental device 10 can be formed of a disposable material. For example, dental device 10 can be formed of a rigid or semi-rigid plastic material. Suitable materials include high density polyethylene (HDPE).

FIG. 2 illustrates a method for registration of an anterior midline and a horizontal plane between central incisors 30 in accordance with the teachings of the present invention. In step 31, body 12 is placed between the upper and lower teeth. Front face 14 extends on the outside of the patient's mouth. The patient bites into registration material 15 on upper surface 16 and lower surface 17 of tab stop section 13. In block 32, as the patient bites down, tab stop section 13 is aligned in a correct position of the patient's middle plane and horizontal plane. The alignment can use the patient's facial landmarks, such as the eyes, nose or lips for determining the correct position. Registration material 15 is allowed to set before dental device 12 is removed from the patient's mouth in block 33. Dental device 10 with set registration material 15 can be sent to a lab along with a final impression, counter model and occlusal bite registration for the fabrication of the crowns and or veneers in block 34.

The lab technician can then use dental device 10 to mark on the model. In block 35, the lab technician can also check the position of formed crowns or veneers by attaching the formed crowns or veneers to the upper portion of the model and removing the registration material 15 from the upper surface of 16 tab stop section 13 in block 36. In block 37, the model and dental device 10 are closed together on an articulator to see if the midline and horizontal plane are correct before returning the crown and/or veneers back to the dentist in block 38.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A dental device comprising:
    a body having a curved end, said body comprises a front face and a tab stop section extending rearwardly of said front face, an upper surface of said tab stop section for receiving a registration material and a lower surface of said tab stop section for receiving a registration material, said registration material being retained on said upper surface and said lower surface by said front face;
    a horizontal cylindrical indicator bar coupled to said curved end via a connecting bar extending from said curved end; and
    a vertical cylindrical indicator bar coupled to said horizontal cylindrical indicator bar, said vertical cylindrical indicator bar extending vertically from said horizontal cylindrical indicator bar, wherein said horizontal cylindrical indicator bar and said vertical cylindrical indicator bar and said connecting bar are monolithic and are integral to one another and form an upside down "T" shape in which said vertical cylindrical indicator bar extends upwardly,
    wherein said dental device is formed of a disposable material.

2. The dental device of claim 1 wherein said body has a "U" shape.

3. The dental device of claim 1 wherein said dental device is formed of plastic or high density polyethylene (HDPE).

4. A kit comprising:
    a dental device comprising:
    a body having a curved end, said body having a front face and a tab stop section extending rearwardly of said front face, an upper surface of said tab stop section and a lower surface of said tab stop section;
    a horizontal cylindrical indicator bar coupled to said curved end via a connecting bar extending from said curved end;
    a vertical cylindrical indicator bar coupled to said horizontal cylindrical indicator bar, said vertical cylindrical indicator bar extending vertically from said horizontal cylindrical indicator bar; and
    a registration material, said registration material being received on said upper surface and said lower surface of said body and retained by said front face, wherein said horizontal cylindrical indicator bar and said vertical cylindrical indicator bar and said connecting bar are monolithic and form an upside down "T" shape in which said vertical cylindrical indicator bar extends upwardly,
    wherein said dental device is formed of a disposable material.

5. The kit of claim 4 wherein said dental device is formed of plastic or high density polyethylene (HDPE).

* * * * *